Figure 4:
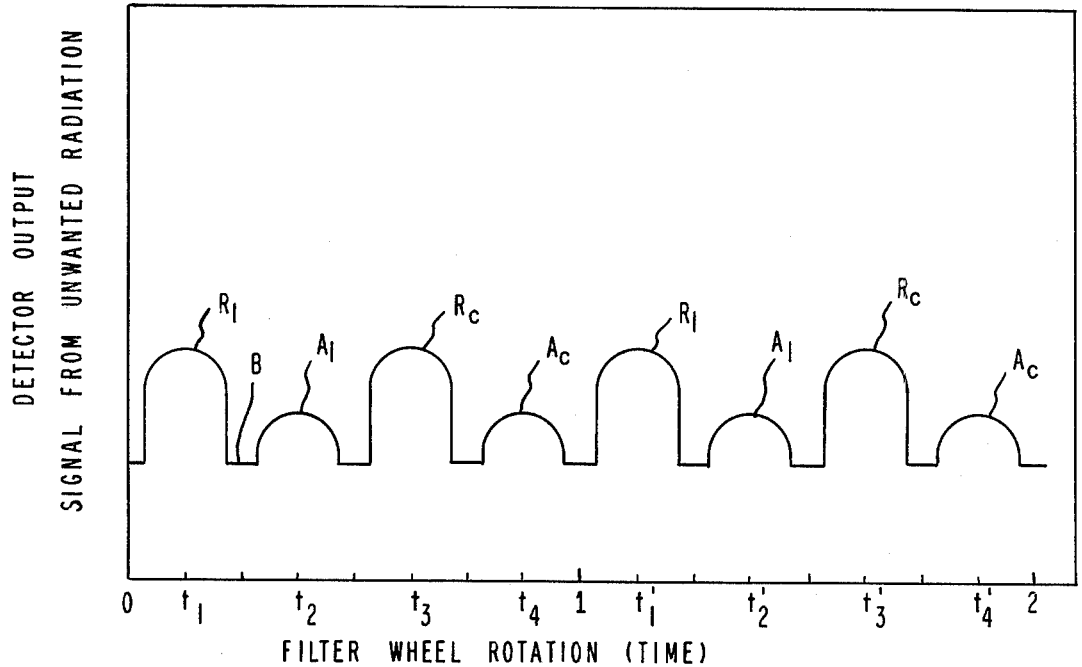

United States Patent [19]

Prober

[11] 4,087,690

[45] May 2, 1978

[54] SPURIOUS RADIATION COMPENSATION IN INFRARED ANALYZERS

[75] Inventor: James Merrill Prober, Wilmington, Del.

[73] Assignee: E. I. Du Pont de Nemours and Company, Wilmington, Del.

[21] Appl. No.: 698,698

[22] Filed: Jun. 22, 1976

[51] Int. Cl.² .................. G01J 1/00; G01N 21/24; G01N 21/26
[52] U.S. Cl. .................. 250/343; 250/351; 250/565; 356/51
[58] Field of Search .............. 250/351, 565, 575, 343; 356/51

[56] References Cited

U.S. PATENT DOCUMENTS

| | | | |
|---|---|---|---|
| 3,392,282 | 7/1968 | Astheimer | 250/351 |
| 3,794,838 | 2/1974 | Weiss et al. | 250/351 |
| 3,955,096 | 5/1976 | Faulhaber | 250/575 |

Primary Examiner—Alfred E. Smith
Assistant Examiner—T. N. Grigsby

[57] ABSTRACT

Method and apparatus for compensating spurious radiation detector signal output variations during operation of an infrared (IR) analyzer.

10 Claims, 18 Drawing Figures

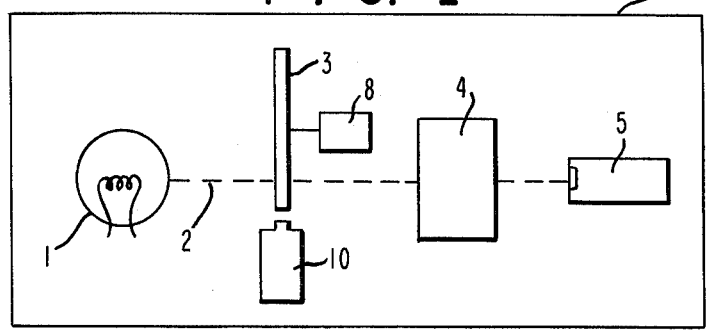
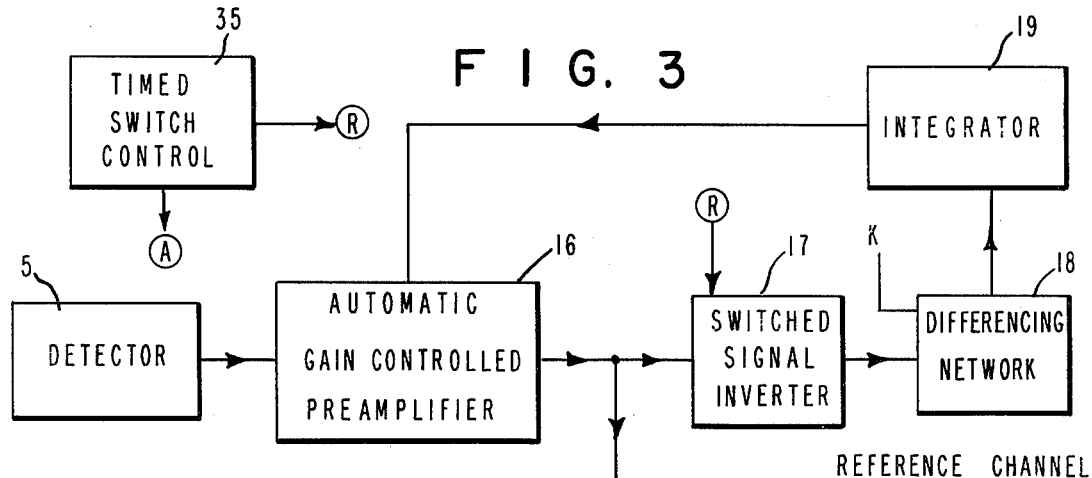
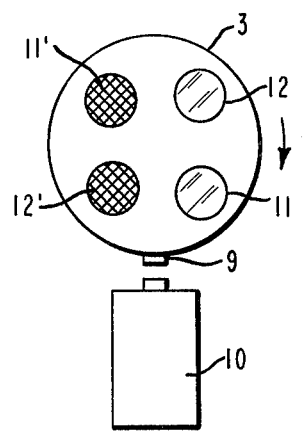

FILTER WHEEL ROTATION (TIME)

SPURIOUS RADIATION COMPENSATION IN INFRARED ANALYZERS

BRIEF SUMMARY OF THE INVENTION

Generally, this invention consists of method and apparatus for compensating infrared radiation photometric analyzers for extraneous infrared radiation contributed by apparatus elements, as distinguished from the analytical and reference radiation signals per se, comprising providing a movable filter support structure interposing individual filters sequentially across the infrared radiation beam with radiation non-transmitting dummy ports of the same size and type as their transmitting counterparts, and electrically cancelling the effects of said extraneous infrared radiation from the individual measured signals of the analytical and reference filters with the outputs contributed by their dummy counterparts during each operating cycle of the movable filter support structure.

BACKGROUND

Infrared analyzers, especially those operating in the mid IR range with wavelengths of about 5–15μ, are subject to changes in performance due to temperature effects. This is due to the fact that objects within the instrument housing give off radiation which will be sensed by the detector.

Analyzers in which the IR radiation is modulated by sequential insertion of filters or masks at timed intervals present a particular problem, in that the detector will sense some of the radiation reflected from and emitted by the filter and mask material per se.

Although this invention is described in application to a high speed rotary filter wheel type IR analyzer provided with reference and analytical optical filters which are interposed across the radiation beam at regular intervals, it can be embodied in filter type photometers broadly, including those using reciprocating filter flag or slide type modulation means. The radiation reflected from, and emitted by, the detector side of the modulating structure varies with temperature and can markedly affect the analyzer output signal, thereby reducing the measuring sensitivity. Mid IR analyzers are particularly susceptible to extraneous (stray) radiation because room temperature black body radiation peaks at a wavelength in the mid-IR range. The effect of such extraneous radiation on analysis is nullified by this invention by making the surface of the filter structure facing the detector as much alike as possible by using radiation non-conducting dummy ports corresponding to their counterpart analytical and reference filters and subtracting preselected detector output signals in a time pattern which exactly cancels out the extraneous radiation effects.

There are several different models of IR analyzers on the market designed to perform on-line analyses. Some of these employ a single beam of IR radiation which is modulated, as by individual radiation-selecting filters, to provide, in rapid sequence, an analytical wavelength for a preselected time interval and a reference wavelength for a different preselected time interval. This modulation can be achieved by mounting optical filters transmitting preselected radiation wavelengths on a support structure effecting interposition of the filters in preselected order at high speed across the radiation path.

It is preferred to utilize the detector analytical signal in ratio with the detector reference signal to give an output signal measuring the relatively fixed concentration of a constituent of interest in the radiation-transmitting sample. The reason for this is that, by using the ratio, the analyzer is rendered significantly less sensitive to factors which affect the signal at both of the reference and analytical wavelengths such as variations in source light level, dirt on the sample cell windows and the like.

The vexatious source of stray (extraneous) radiation sensed by the detector is that emitted by, or reflected from, the surface of the filter structure. This will not be a steady radiation source but will change, depending on what part of the filter structure is instantaneously viewed by the detector.

In the present state of the art several methods are now in use for temperature accommodation of mid-IR analyzers. One obvious way is to carefully control the temperatures of all sources of radiation which the detector might sense. This is an extremely costly way of eliminating the problem.

Another approach is to periodically have the analytical instrument recalibrated for baseline and span by the automatic insertion of the proper standard samples. This, too, is expensive and, besides, breaks the continuity of the analysis.

A principal object of this invention is to provide a method of temperature compensation which is inexpensive and does not reduce the sensitivity of the analyzer.

DRAWINGS

The following partially schematic drawings illustrate two embodiments of this invention, in which:

FIG. 1 is a schematic plan view of a conventional rotary filter wheel type infrared photometric analyzer, FIG. 2 is a side elevation view of the filter wheel of the analyzer of FIG. 1 showing also the associated magnetic wheel rotation sensor, with four port symmetrical placement according to this invention.

Figure 5:
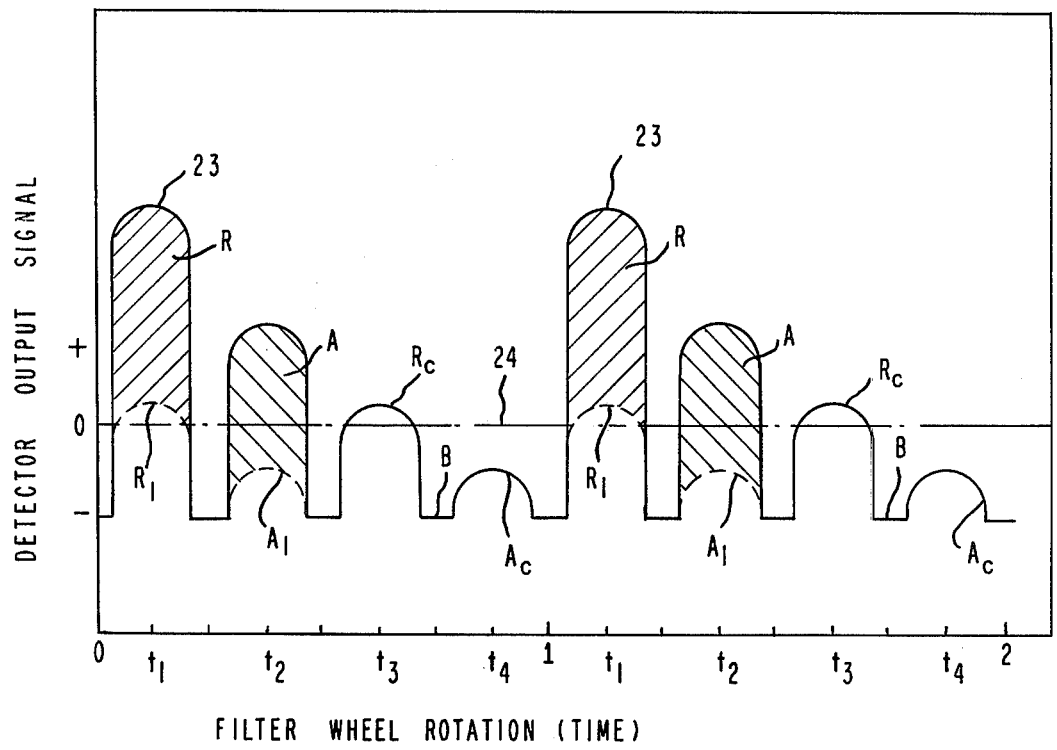
Figure 6A:
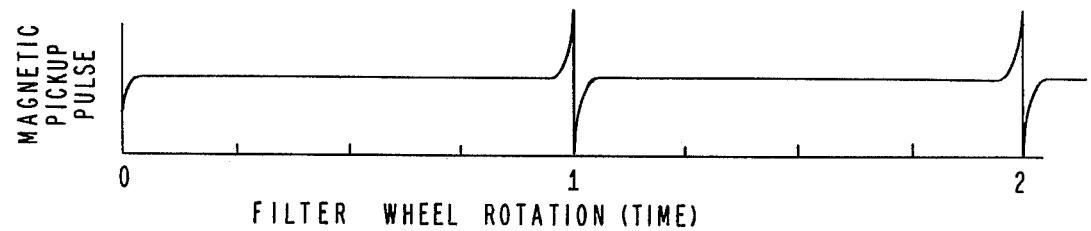
Figure 6B:
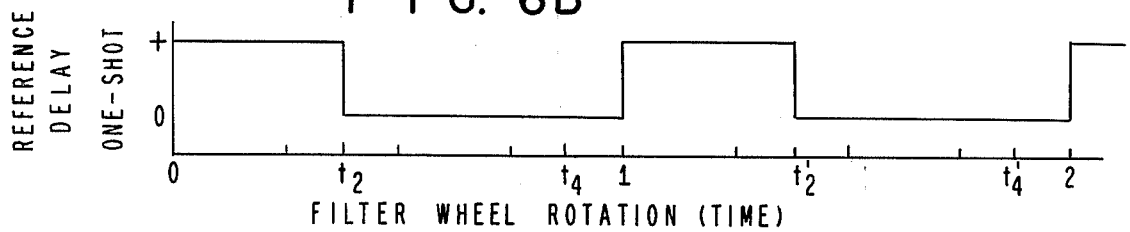
Figure 6C:
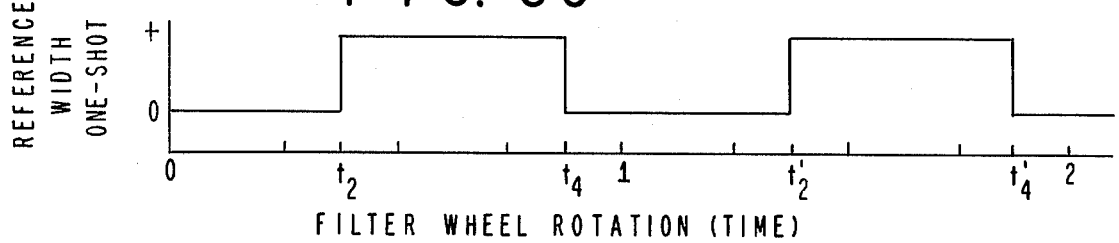
Figure 6D:
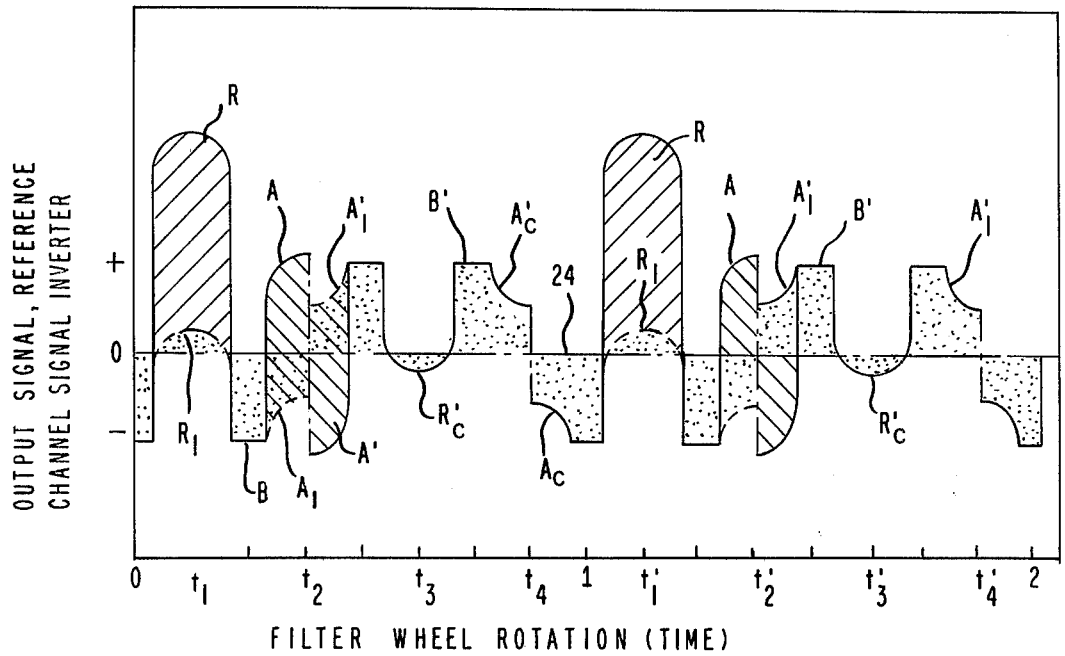
Figure 6E:
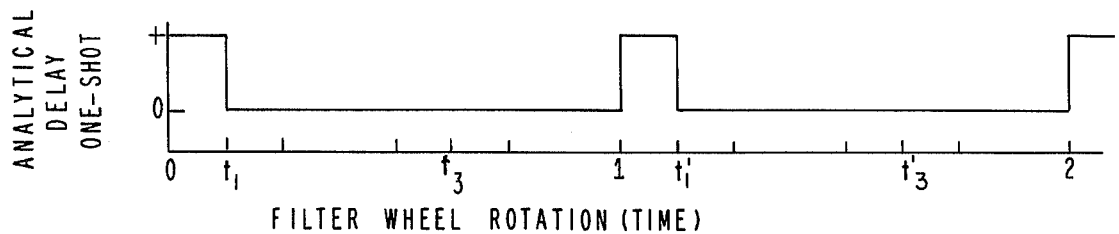
Figure 6F:
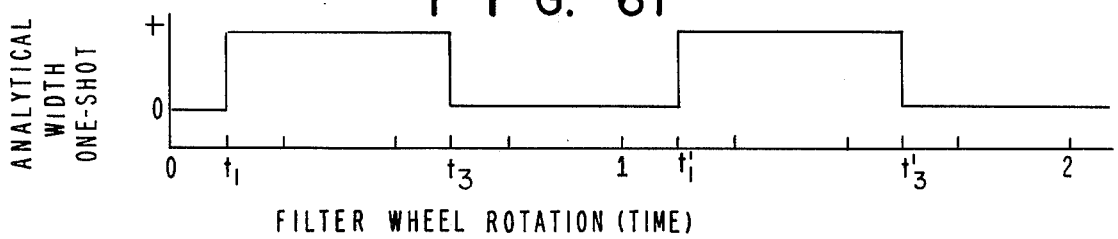
Figure 6G:
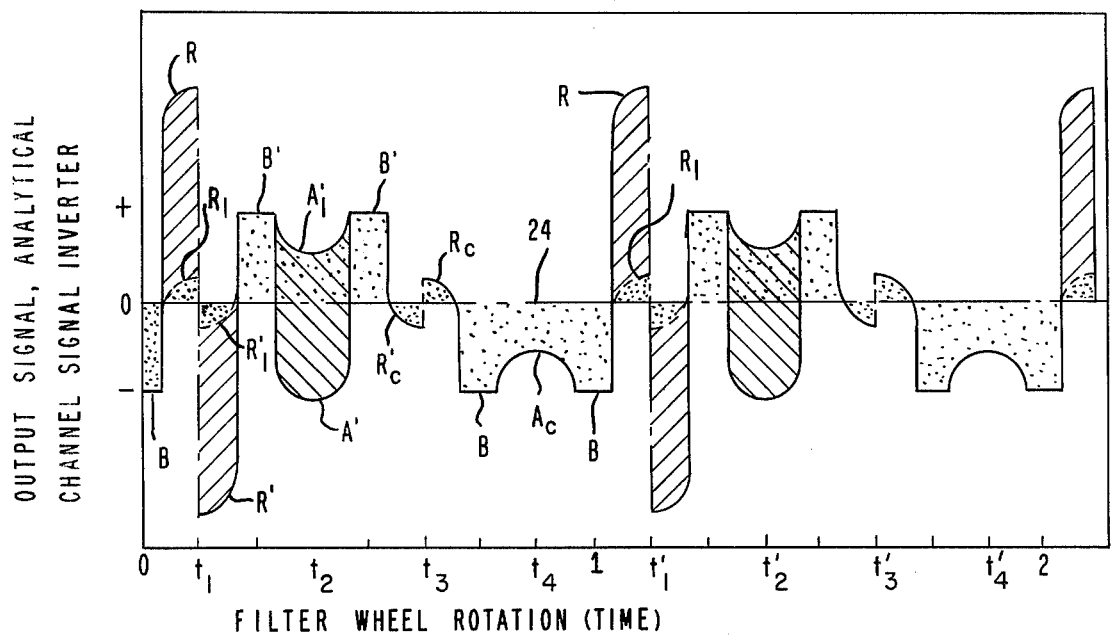
Figure 7:
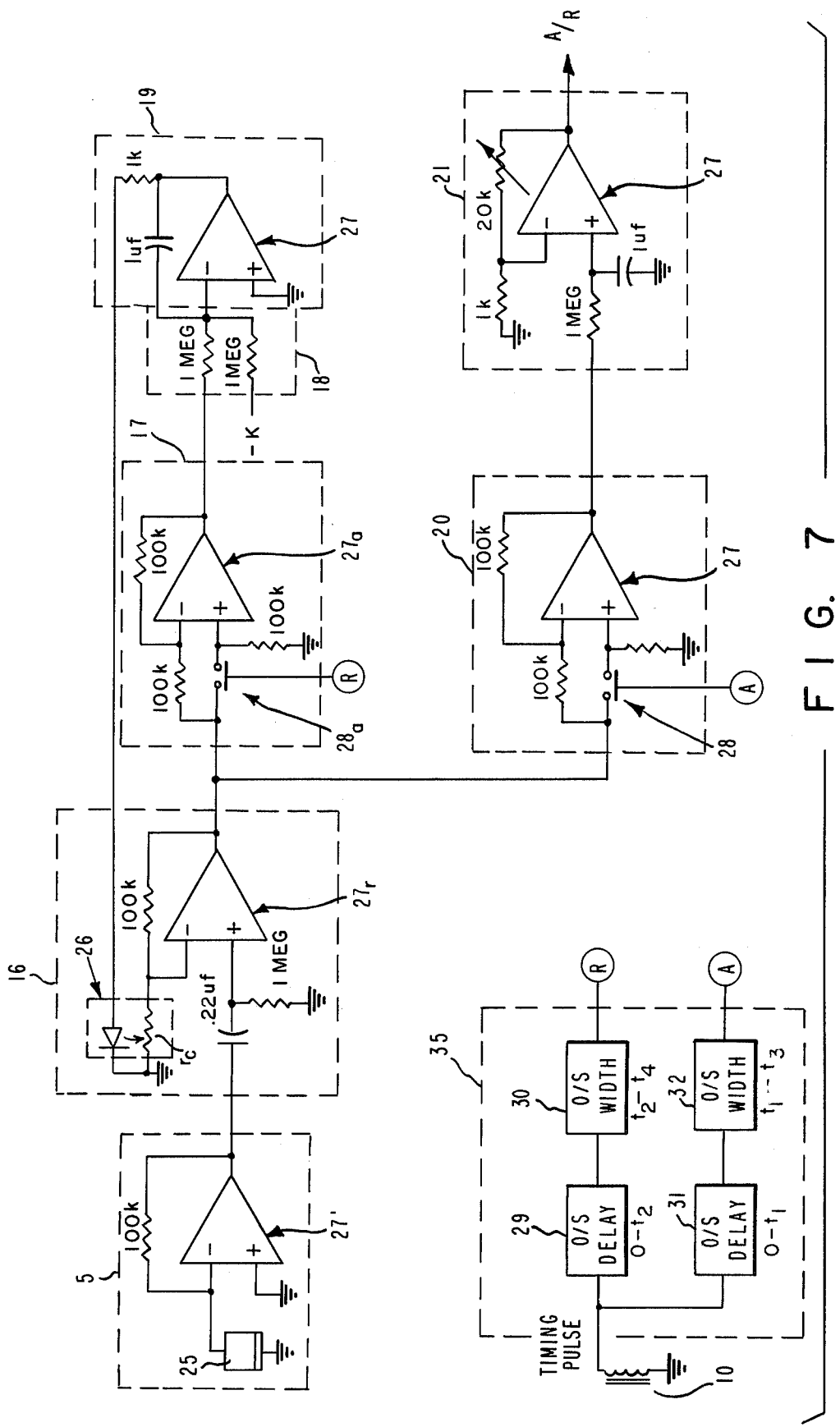
Figure 8:
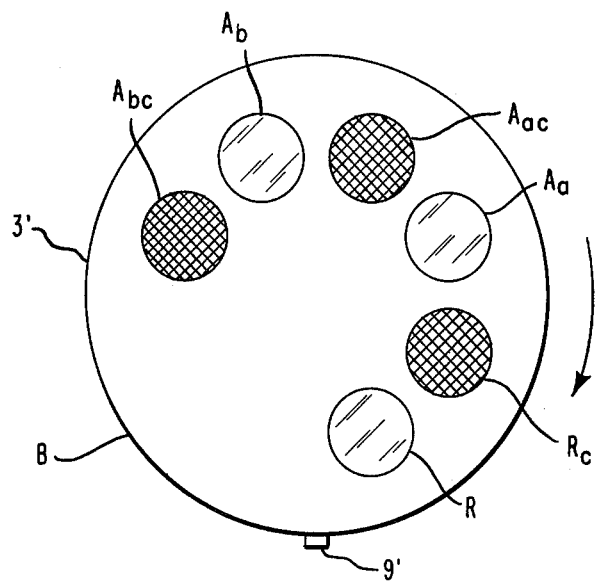
Figure 9:
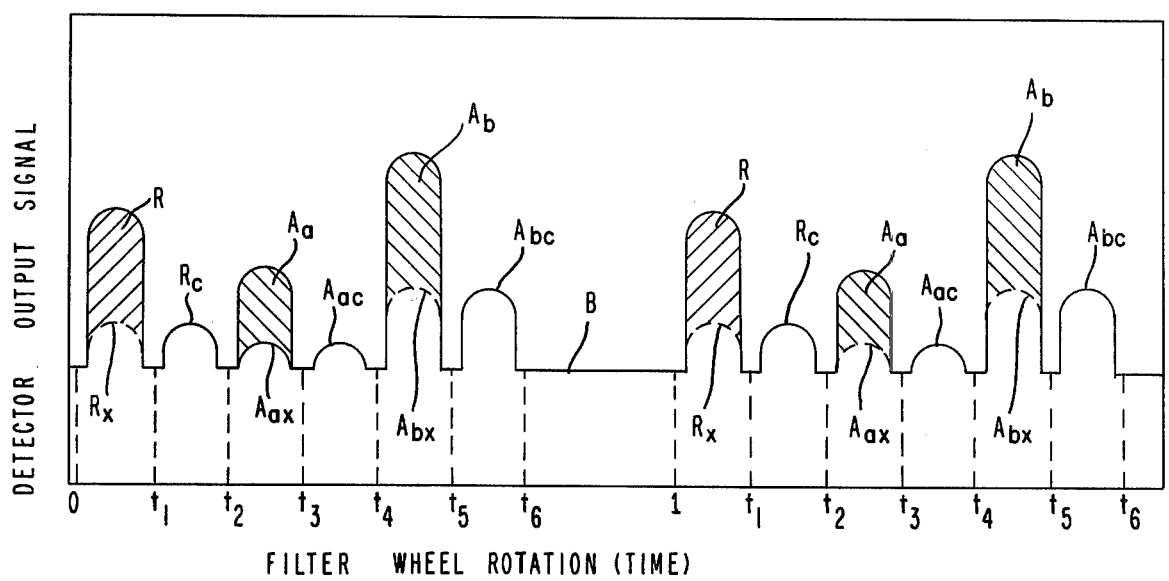
Figure 11:
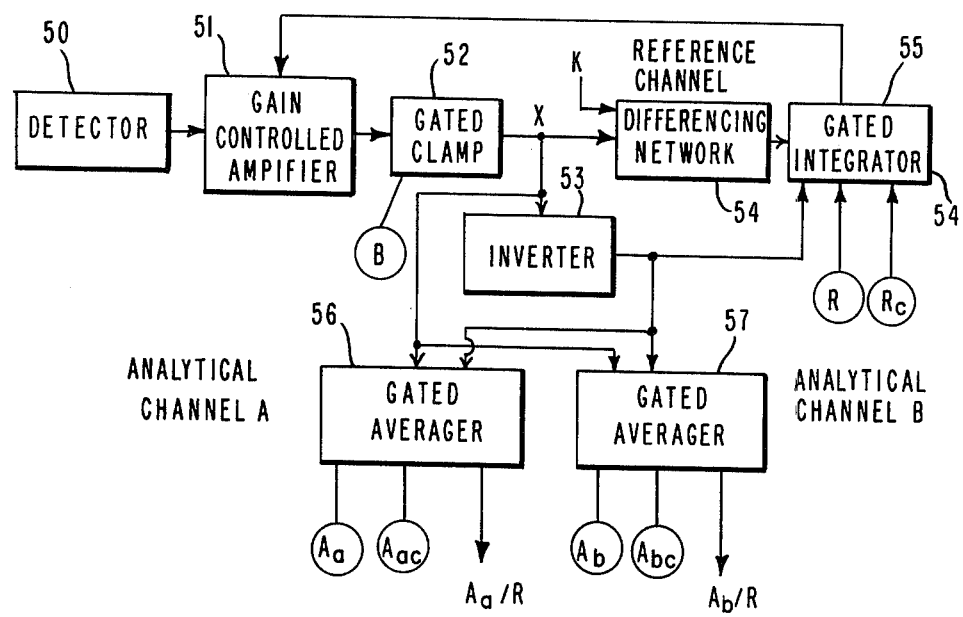
Figure 10:
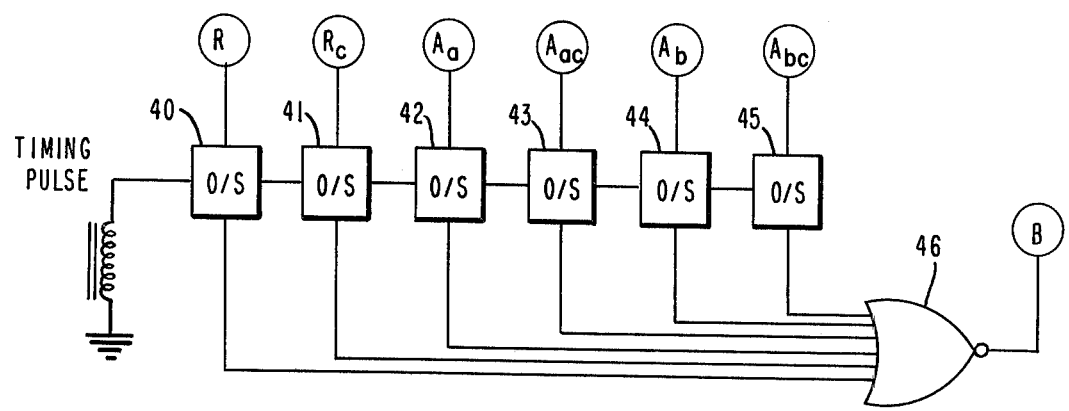
Figure 12:
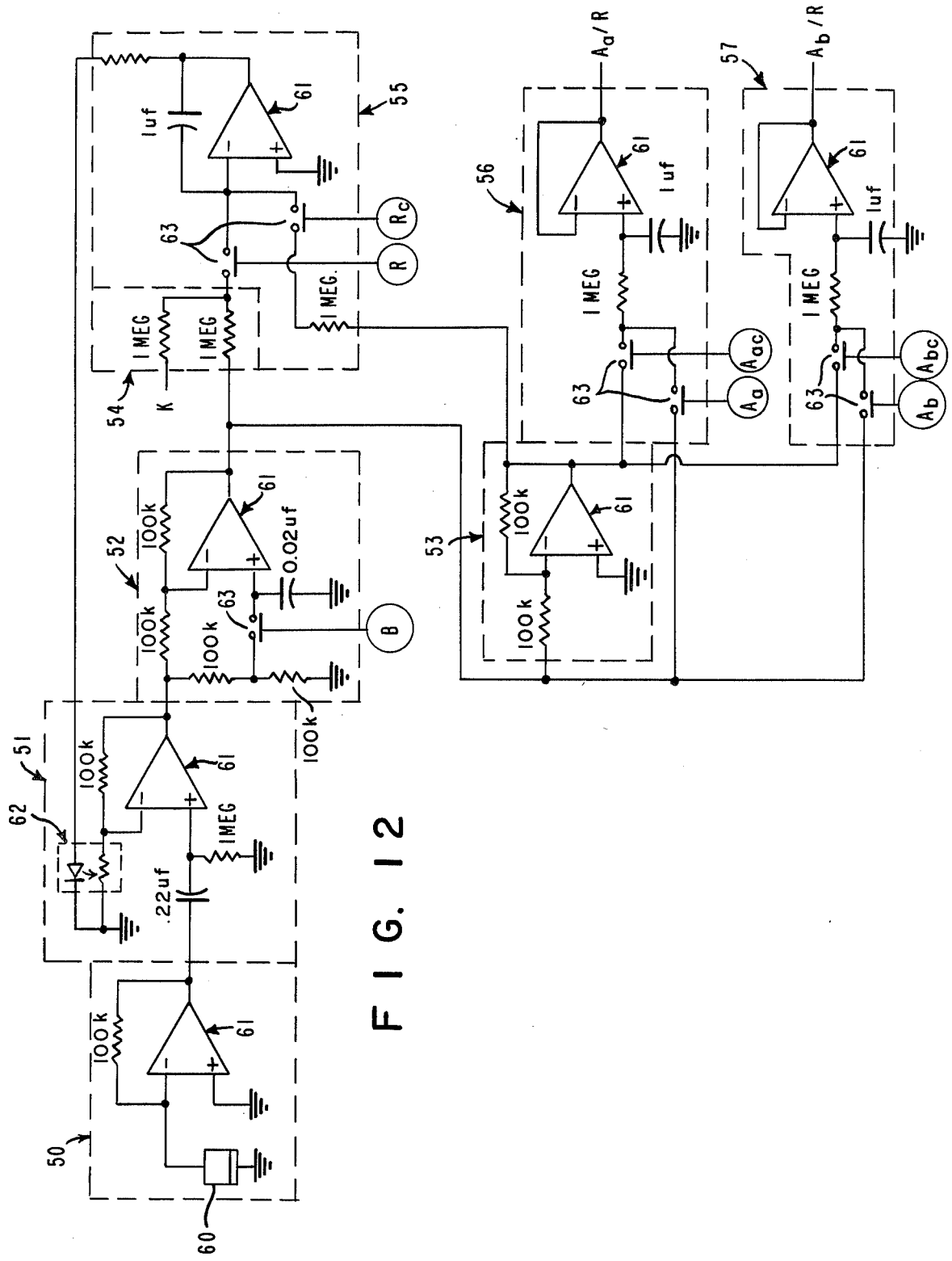

FIG. 3 is a block diagram of the electric circuitry utilized in the FIGS. 1 and 2 embodiment of this invention, FIG. 4 is a schematic electrical pulse sequence output (magnitude v. time) of the detector of FIG. 1 during filter wheel rotation with all four ports blocked on the source side against radiation passage but with the sample cell filled with sample in place athwart the radiation beam, FIG. 5 is a schematic electrical pulse sequence output exactly like FIG. 4, except with the analytical and reference ports uncovered but the dummy ports still blocked, FIGS. 6A, 6B and 6C are, respectively, pulse-time diagrams for the filter wheel magnetic trigger pulse and the delay and width one-shot switch gating pulses generated by the trigger pulse and supplied in cyclic sequence to the Reference Channel of FIGS. 3 and 7, FIG. 6D is a plot of the output signal from the FIGS. 1–4 apparatus embodiment Reference Channel signal inverter v. filter wheel rotation (time) showing the compensating cancellation of all radiation signal output except the desired Reference Signal, FIGS. 6E and 6F are, respectively, pulse-time diagrams for the analytical delay and analytical width one-shot switch gating pulses generated by the filter wheel trigger pulse and supplied in cyclic sequence to the Analytical Channel of FIGS. 3 and 7, FIG. 6G is a plot of the output signal from the Analytical Channel signal inverter of the apparatus of FIGS. 1-4 showing the compensating cancellation of all radiation signal output except the desired Analytical Signal, FIG. 7 is a schematic electrical circut for the FIGS. 1-4 embodiment of this invention, FIG. 8 is a side elevation view of the filter wheel of a second embodiment of this invention, FIG. 9 is a schematic electrical pulse sequence output (magnitude v. time) of the embodiment of FIG. 8 during filter wheel rotation with the three dummy ports blocked whereas the analytical and reference ports are uncovered, FIG. 10 is a schematic representation of the time sequencing sub-assembly for the apparatus of the second embodiment, FIG. 11 is a block diagram of the second embodiment of this invention, and FIG. 12 is a schematic electrical circuit for the second (FIGS. 8-10) embodiment of this invention.

THE INVENTION

A preferred embodiment of this invention utilizing a filter wheel operates by coupling the frequency of electrical signal inversion from the detector to the frequency of the filter wheel in such a way that inversion occurs every one-half revolution of the wheel and, by making the wheel 180° symmetric in reflectance and sensitivity, the effects of stray radiation from or off of the filter wheel are cancelled. At the same time, the analytical and reference signals are processed once per cycle, but in separate channels, so that they are individually preserved and not nullified.

This can be accomplished by providing a radiation-non-transmitting twin dummy filter at the same center-to-center radii from the axis of rotation and exactly 180° around from each modulation filter in the filter wheel required for analysis. The combined radial and angular disposition described is hereinafter comprehended collectively by the term "symmetric." These twin dummy filters should be of the same size and should be provided with filter materials of the same compositions as their counterparts, except that they are backed with an opaque insert as denoted by the cross hatching, on the side away from the detector, so that they reflect and emit stray radiation equally as their paired optical counterparts but the IR source radiation is not transmitted by them. Filter wheels according to this embodiment can accommodate any number of reference and analytical filters, so long as identical dummy filters with opaque backing on the source side are placed 180° symmetric to them. This filter wheel arrangement is also advantageous from the standpoint of changing filters without affecting temperature compensation, because all one has to do is to change the filters in 180° symmetry as well.

Referring to FIGS. 1 and 2 there is shown the optical arrangement of a continuous IR analyzer employing a single modulated beam. The IR radiation is provided by the radiation source 1, which can be a tungsten filamentary lamp having a window (e.g., IRTRAN®-3, which is polycrystalline calcium fluoride) designed to transmit radiation in the desired wavelength range.

The radiation beam 2 passes down the broken line path of FIG. 1 through the transmitting filters of filter wheel 3 and thence through the sample cell 4 to the conventional detector 5 (which is preferably a pyroelectric detector; however, a photovoltaic detector can be utilized, such as PbSe or InSb).

In FIG. 1 the radiation-transmitting sample cell 4 is intended to contain a fixed or continuously flowing fluid sample; however, the cell can be replaced by solid samples if this is the material to be analyzed. All of the optical elements are housed in a radiation-tight housing denoted generally at 6. For purposes of simplicity in the showing, lenses, mirrors and other components which are usually required for focusing and changing radiation beam direction are omitted.

Filter wheel 3 is rotated by drive means 8, which is usually a synchronous electric motor. Filter wheel 3 is usually fabricated from a non-magnetic material, such as aluminum, and is provided with a thin iron slug 9 on the periphery. Slug 9 induces an electrical pulse in electromagnetic pickup 10, spaced therefrom at, typically, 0.002 ± 0.001 inch clearance, which provides a time reference for the electronic circuitry hereinafter described, which routes the reference and analytical signals through the channels and also provides a time reference for controlled inversion of the detector signals once each half revolution of filter wheel 3.

The filter wheel shown in FIG. 2 has an analytical radiation wavelength filter 12 and a reference radiation wavelength filter 11. Symmetric thereto on the same radii and at 180° spacings therefrom are the identical dummy filters 11' and 12', which are covered with opaque inserts on the source side so that they are radiation non-transmitting. This provides a filter wheel which is correspondingly symmetric in reflectance and emissivity of extraneous radiation on the detector side.

Filter wheel 3 can be driven at any speed; however, it is advantageous to drive it at 1800 rpm, which is 30 cycles/sec. Since the electrical signal from detector 5 will be inverted for one half of each revolution of the filter wheel, the reversal will occur 60 times per second. Reversal at this particular frequency is advantageous since it cancels any 60 cps noise, which is of common occurrence.

Referring to FIG. 3, the circuit block diagram, all of the components of the electronic circuit are commercially available items.

As indicated, the circuit provides separate channels for the compensated Reference (R) and Analytical (A) determinations.

The signal from detector 5 is passed directly to a preamplifier 16 in which the gain is automatically controlled to drive the reference portion of the signal toward a preselected constant value. Preamplifier 16 is a-c coupled, so that any d-c signal generated by the detector does not pass through. In this way signals from slowly changing sources of radiation seen by the detector which are not modulated are eliminated.

The signal exiting preamplifier 16 goes to two separate channels, a reference channel and an analytical channel.

The reference channel comprises a switched signal inverter 17 actuated by gating signal Ⓡ which is derived from operation of one-shots 29 and 30 (FIG. 7) of timed switch control 35 and electromagnetic pickup 10. The switch of inverter 17 is phased appropriately as described infra, so that any signals entering, other than the true reference signal, average to zero when the pulse sequence is integrated by integrator 19 over a number of complete rotations of filter wheel 3.

The next reference channel operation on the signal is the subtraction, in differencing network 18 (FIG. 7), of a constant reference signal K, followed by integration of the resultant difference in integrator 19. Thus, reference signal R is effectively compared with a constant K by subtraction and the integrated difference is returned as a feedback for automatic gain-controlled preamplifier 16. At equilibrium, the reference signal R is equal to K. Thus, R is always driven toward a constant predetermined value.

The second, or analytical channel, comprises a switched signal inverter 20, generally similar to inverter 17 in the reference channel, and a signal averaging device 21. Gating signal (A) is phased via one-shots 31 and 32 (FIG. 7) so that all but the true analytic signal input in the pulse sequence is nullified when time averaged, by averager 21, over a number of complete cycles of filter wheel 3. Both signal inverters 17 and 20 are phased so that their processed signals are effectively multiplied by +1 for one half of the filter wheel cycle and by −1 for the other half of the filter wheel cycle. By phasing in this way, any stray radiation emitted from or reflected off filter wheel 3 is nullified. Since filter wheel 3 is constructed to be symmetric about its axis of rotation, the unwanted signal from it will be the same every one-half cycle.

For example, referring to FIG. 4, which portrays the waveform sensed by detector 5 in the situation where sample cell 4 containing sample to be analyzed is interposed athwart the radiation beam but all four ports 11, 12, 11′ and 12′ are blocked against radiation passage, it is seen that the filter wheel 3 constructional symmetry results in sequential signals, alternate ones of which are equal. Thus, signal B consists of radiation emitted by and reflected from metal filter wheel 3. $R_1$ represents radiation received from reference filter 11, $A_1$ for that from analytical filter 12, $R_c$ for that from dummy filter 11′ 180° symmetric to reference filter 11 and $A_c$ for that from dummy filter 12′ 180° symmetric to analytical filter 12. It can be seen that very substantial extraneous radiation is inevitably sensed by detector 5, even when it is completely blocked from the radiation source.

Now, if the two ports 11 and 12 are uncovered, but the dummy ports 11′ and 12′ remain blocked, the detector will immediately receive radiation from source 1 via filters 11 and 12 which will be additive to the radiations $R_1$ and $A_1$ of FIG. 4 and are thus shown as cross-hatched increments (with boundary indicated by line 23) superposed on these waveforms in the representation of FIG. 5. Line 24 is simply the average signal output level, drawn in to permit better visualization of the compensation obtained with this invention.

The objective of the reference channel is to obtain a reference signal free of any other signal incursions above or below the base line 24. Accordingly, referring to FIG. 6D, the signal is inverted (i.e., multiplied by −1) starting at time $t_2$, which is, for this example, a time corresponding to the peak value of signal A and ending at time $t_4$, corresponding to the midpoint of the signal derived from the analytical compensation dummy filter 12′. As required to achieve nullification of unwanted signals from the signal wheel, the inversion is maintained for exactly one-half of a filter wheel 3 rotation. Precisely at time $t_4$, the signal reverts to its original uninverted state (i.e., as multiplied by +1). One can see from the dot convention areas of FIG. 6D, that the radiation constituting the signals originating from stray radiation from filter wheel 3 (e.g., B, $A_1$, $A_c$ and $R_1$) are exactly cancelled by their counterparts (B′, $A_1'$, $A_c'$ and $R_c'$, respectively). (Since it is desired to obtain the reference, R, and analytical signal, A, free of each other, in their separate channels, these are also cancelled by the inversion technique, the cancellation of A being indicated in FIG. 6D whereas the cancellation of R is shown in FIG. 6G.)

Operation of the analytical channel is portrayed in FIGS. 6E–6G, FIG. 6E showing the high level delay pulse ($0-t_1$) for the delay one-shot (31, FIG. 7) with the gating pulse (A) transmitted during time interval $t_1-t_3$ by the width one-shot (32, FIG. 7) as shown in FIG. 6F. As FIG. 6G shows, the signal R is eliminated by inversion cancellation in the same manner as the spurious radiation values B, $A_c$, $R_1$ and $R_c$ as indicated by their respective counterparts B′, $A_1'$, $R_c'$ and $R_1'$, so as to preserve the analytical radiation A′ solely in the analytical channel.

Turning now to the detailed circuit of FIG. 7, the radiation detector 25, provided with its own current-to-voltage transforming amplifier 27′, is drawn in the convention of a photovoltaic cell, the six differential operational amplifiers 27′, $27_r$, $27_a$ and 27 can all be Teledyne-Philbrick 142602 types, the gated switches 28a, 28 can be FET switches equivalent to Silconix DG200BA, and the one-shots 29–32 can be Signetic NE555V. The feedback indicated generally in FIG. 7 utilizes a light-sensitive resistor $r_c$ in conjunction with a light-emitting diode, the entire unit being marketed as a Clairex CLM 6000 denoted 26. This feedback is detailed in U.S. Pat. No. 3,955,096, of common assignment herewith, together with the implicit ratioing by which the circuit of FIG. 7 delivers the desired ratio A/R from the analytical channel. The respective values of resistance and capacitance are indicated adjacent the several other circuit components of FIG. 7.

The operation of the circuit of FIG. 7 is straight-forward, and therefore not described further herein, except as regards switched signal inverter 17.

Inverter 17, reserved to the processing of the reference signal R, has its input coupled to both the inverting and the non-inverting inputs of differential operational amplifier 27a. The coupling to the inverting (−) terminal is via a 100 Kohm resistor whereas the coupling to the non-inverting (+) terminal is via the electronic switch 28a which is closed when its control terminal is at a logic low voltage level. The "on" resistance of switch 28a is negligible compared to the resistors of the circuit.

Amplifier 27a, by feedback, forces the inverting terminal to equal the potential at the non-inverting terminal. When the switch control terminal is at logic high, i.e., during the time interval $t_2$ to $t_4$, FIG. 6C, switch 28a is open and the non-inverting (+) amplifier terminal is at ground potential. With switch 28a open, amplifier 27a becomes an inverting amplifier and its input is effectively multiplied by −1 at the amplifier output. Conversely, when the switch control terminal, FIG. 6C, is at logic low, switch 28a is closed and the non-inverting terminal of amplifier 27a is at input signal potential. The amplifier, through feedback, forces the inverting (−) terminal also to input signal potential. Thus, there is no current flow in the coupling resistor or the feedback resistor and the output of the amplifier becomes equal to the input multiplied by +1.

The output of time-switched signal inverter 17 is a net positive voltage signal R containing only the desired reference components. This signal R is current-summed in differencing network 18 with a constant negative potential −K.

The net current, R-K, is integrated by integrator 19, which delivers the integrated signal as feedback to control the gain of amplifier 27, as hereinbefore described.

The output of time-switched signal inverter 20 is a net negative signal containing only desired analytical components. This A signal is smoothed (averaged) and amplified by averager 21. Since the system gain is regulated by feedback to hold R constant, the output from 21 becomes, by implicit ratioing, proportional to the quantity A/R.

EXAMPLE

A mid-IR analyzer was operated during warm up with and without, a filter wheel possessing 180° symmetry according to the first embodiment of this invention. The apparatus, employing a filter wheel 3 of the general design shown in FIG. 2, was tested in comparative runs made with an empty sample cell in the radiation beam. The analyzer employed a tungsten filament lamp designed for service at 6 volts and 6 amperes, but operated at only 5 volts, as radiation source 1, utilizing an IR-TRAN®-3 window. The filament was operated at 1600° C.

The filter wheel 3 was an aluminum wheel about 3 inches dia. driven by an 1800 rpm synchronous motor 8. Two one-inch dia. radiation modulating optical filters 11 and 12 were placed at 90° to one another on an otherwise solid filter wheel 3. These were the reference filter 11 and the analytical filter 12.

The signal from the electromagnetic pickup 9, 10 triggered the pulses shown in FIGS. 6A–6C and 6E, 6F so that the signal from detector 5 was inverted every half revolution of filter wheel 3. The A/R signals were obtained as output from averager 21.

After startup and with no opaque backing on the source side of wheel 3, the temperature in housing 6 rose from 30° C to 46.5° C, whereupon the output voltage of the averager 21 dropped by about 20%, which was equivalent to about 0.005 absorbance unit per ° C.

When filter wheel 3 was fitted with like blocked filters 11' and 12', symmetrically disposed with respect to the reference and analytical filters 11 and 12, respectively, with blocking applied to the source side of wheel 3, the output voltage signal from averager 21 dropped less than 2% for a temperature rise of 11° C. This was equivalent to less than 0.0005 absorbance unit per ° C. Thus, there was achieved a ten-fold decrease in temperature sensitivity, thereby enhancing the analyzer's overall measuring sensitivity correspondingly.

It will be understood that, although the inversion cancellation removal of modulated analytical radiation from the reference channel and modulated reference radiation from the analytical channel is a convenience, this invention is not limited by this feature.

Thus, it is practicable, by proper gating, as taught in U.S. Pat. No. 3,955,096 hereinbefore referred to, to first separate the reference and analytical signals and thereafter compensate for $R_1$ and $A_1$ using this invention.

SECOND EMBODIMENT

While the spatial symmetrical opposition of dummy and radiation modulating (or optical) filters utilized in the first embodiment supra is preferred, for best-spaced time utilization, this is not essential as regards filter angular placement particularly.

Thus, FIG. 8 shows a filter wheel 3' provided, all at equal radii, with three optical filters, R, $A_a$ and $A_b$, and three dummy filters, $R_c$, $A_{ac}$ and $A_{bc}$, each disposed adjacent its counterpart. With this arrangement each optical filter together with its counterpart occupies about one quarter of the wheel 3' surface. Under these circumstances, as shown in FIG. 9, the extraneous radiation sensed by the detector when the optical filters R, $A_a$ and $A_b$, respectively, are in the path of source radiation will be $R_x$, $A_{ax}$ and $A_{bx}$, respectively.

Cancellation of the effects of extraneous radiation in the signal from the detector is achieved by the circuit of FIGS. 10 and 11. Time coordination with filter wheel rotation is achieved by the series of one-shots shown in FIG. 10, the first one of which 40, outputting gating signal Ⓡ, is set off by the timing pulse signal from filter wheel 3' rotation. The other one-shots (41, 42, 43, 44 and 45) are triggered consecutively with preselected durations such that each one-shot brackets an individual gating signal such as Ⓡ$_c$, Ⓐ$_a$, Ⓐ$_{ac}$ and so forth. Thus, one-shot 40 produces a gating pulse Ⓡ for the time period 0 to $t_1$, (FIG. 9), one-shot 41 produces a gating pulse Ⓡ$_c$ for the time period $t_1$ to $t_2$, one-shot 42 produces a gating pulse Ⓐ$_a$ for the period $t_2$ to $t_3$, and so on. Outputs are taken from the one-shots during their "on" periods and are supplied to NOR gate 46 so that, when no pulse is present on any of the input lines to NOR gate 46, it produces an output pulse Ⓑ.

The seven control gating pulses denoted by encircled letters, i.e., Ⓡ, Ⓡ$_c$, Ⓐ$_a$, etc, are utilized as indicated in the block diagram, FIG. 11.

The signal from photovoltaic detector 50 is fed to a gain-controlled amplifier 51. As in the Example reported supra, amplifier 51 is gain-controlled by feedback from the reference channel, so that the reference signal R is kept at a constant value. The output from gain-controlled amplifier 51 passes to a gated clamp circuit 52 which acts to make the signal at point X in the circuit zero when control pulse Ⓑ is on. This effectively removes the background signal B so that the remaining electronics senses only the optical and dummy signals shown in FIG. 9 having magnitudes greater than background level B. From point X the signal goes to each of the three channels to be processed. The signal also passes to an inverter 53 where it is effectively multiplied by −1. The inverted signal from inverter 53 also passes to each of the channels to be processed.

In the reference channel R + $R_x$ is processed, along with inverted signal $R_c$, and is compared with constant K. The output from this channel is $$\int_0^t [(R + R_x) - R_c - K] \, dt.$$

Since $R_x = R_c$, the output is integrated difference R−K, which is used to drive the gain-controlled amplifier 51 until R is forced to equal K.

In the analytical channels in this instance (FIG. 11) denoted A and B, respectively, the optical signal $A_a$ + $A_{ax}$ (or $A_b$ + $A_{bx}$, as the case may be) is processed along with the inverted dummy signal $A_{ac}$ (or $A_{bc}$). The outputs are then $_{Avg.}[A_a + A_{ax} - A_{ac}]$ and $_{Avg.}[A_b + A_{bx} - A_{bc}]$, respectively. Since $A_{ax} = A_{ac}$ and $A_{bx} = A_{bc}$, the outputs are the desired signals $A_a$ and $A_b$. Because R is maintained constant, the outputs are proportional to $A_a/R$ and $A_b/R$. Extraneous radiation values $R_x$, $A_{ax}$ and $A_{bx}$ have been cancelled by appropriate use of the dummy filter ports according to this invention.

FIG. 12 is a detailed, somewhat schematic, circuit diagram corresponding to the block diagram of FIG.

11. The operational amplifiers 61 can all be Teledyne-Philbrick 142602 types, whereas the gated switches 63 can all be FET switches equivalent to Siliconix DG200BA. The detector element 60 is a photovoltaic cell. The feedback circuit utilizes a Clairex CLM 6000 unit denoted 62, whereas the one-shots in FIG. 10 can all be Signetic NE 555V types.

While the foregoing embodiments each employ rotary filter wheels as modulating structures, it will be understood that reciprocatory filter support structures such as pivotal flags or linear slides are equally practicable. With such substitutions it is only necessary that the filter counterpart pairs be positioned on the support structures in such a way that each pair member intercepts equal time intervals in the detector viewing area during each complete viewing cycle.

In addition, each of the signal analysis circuits of FIGS. 3, 7, 11 and 12 utilizes signal inverters for effecting subtraction of the extraneous radiation increments from the composite reference or analytical signals. However, it is equally practicable to use a differential amplifier in each channel to perform the necessary differencing function.

For example, referring to the Analytical Channel A in FIGS. 11 and 12, two gated averagers can be used to extract the average signal $_{Ave.}[A_a + A_{ax}]$ and the average signal $_{Ave.}[A_{ac}]$ from the signal at point X, FIG. 11. These output signals can then be differenced by a differential amplifier to produce the compensated analytical signal. In this design no inversion of signals occurs but the necessary compensation is still achieved.

Finally, while this invention has, for purposes of simplicity, been described with reference to a single beam infrared photometric analyzer, it is equally applicable to double beam designs such as that taught in application Ser. No. 670,079 of common assignment.

What is claimed is:

1. The method of compensating infrared radiation photometric analyzers for extraneous infrared radiation contributed by apparatus elements, as distinguished from the analytical and reference radiation signals per se, comprising providing a movable filter support structure interposing individual filters sequentially across the infrared radiation beam with radiation non-transmitting dummy ports of the same size, type and composition as their transmitting counterparts blocked with an opaque material on the analyzer source side, and electrically cancelling the effects of said extraneous infrared radiation from the individual measured signals of the analytical and reference filters with outputs contributed by their dummy counterparts during each operating cycle of said movable filter support structure.

2. In an infrared radiation photometric analyzer compensated for extraneous infrared radiation contributed by apparatus elements, as distinguished from the analytical and reference radiation signals per se, the provision of a movable filter support structure interposing individual filters sequentially across the infrared radiation beam having radiation non-transmitting dummy ports of the same size, type and composition as their transmitting counterparts blocked with an opaque material on the analyzer source side, and means electrically cancelling the effects of said extraneous infrared radiation from the individual measured signals of the analytical and reference filters with the outputs contributed by their dummy counterparts during each operating cycle of said movable filter support structure.

3. The method of compensating rotary filter wheel type infrared radiation photometric analyzers for extraneous infrared radiation contributed by apparatus elements, as distinguished from the analytical and reference radiation signals per se, comprising providing said rotary filter wheel with radiation non-transmitting dummy ports of the same size, type and composition as their transmitting counterparts disposed generally co-radially of said filter wheel, blocked with an opaque material on the analyzer source side, and electrically inverting and opposing individual measured signals of successive analytical and reference filters with the outputs contributed by their dummy counterparts during each full rotation of said rotary filter wheel to thereby cancel the effects of said extraneous infrared radiation.

4. In a rotary filter wheel type infrared radiation photometric analyzer compensated for extraneous infrared radiation contributed by apparatus elements, as distinguished from the analytical and reference radiation signals per se, the provision in said rotary filter wheel of radiation non-transmitting dummy ports of the same size, type and composition as their transmitting counterparts disposed generally co-radially of said filter wheel, blocked with an opaque material on the analyzer source side, and means electrically inverting and opposing signals of successive analytical and reference filters with the outputs contributed by their dummy counterparts during each rotation of said rotary filter wheel to thereby cancel the effects of said extraneous infrared radiation.

5. The method of compensating rotary filter type infrared radiation photometric analyzers for extraneous radiation contributed by apparatus elements according to claim 3 wherein preselected modulated reference or analytical radiation signals are also cancelled by electrical inversion and opposition techniques.

6. Apparatus according to claim 4 provided with means for cancelling a preselected one of the reference and analytical radiation components by electrical inversion and opposition techniques.

7. The method of compensating rotary filter wheel type infrared radiation photometric analyzers for extraneous infrared radiation contributed by apparatus elements, as distinguished from the analytical and reference radiation signals per se, comprising providing said rotary filter wheel with radiation non-transmitting dummy ports of the same size, type and composition as their transmitting counterparts disposed 180° symmetrically opposite thereto, blocked with an opaque material on the analyzer source side, and electrically inverting and opposing individual measured signals of successive analytical and reference filters with the outputs contributed by their dummy counterparts during each full rotation of said rotary filter wheel to thereby cancel the effects of said extraneous infrared radiation.

8. In a rotary filter wheel type infrared radiation photometric analyzer compensated for extraneous infrared radiation contributed by apparatus elements, as distinguished from the analytical and reference radiation signals per se, the provision in said rotary filter wheel of radiation non-transmitting dummy ports of the same size, type and composition as their transmitting counterparts disposed 180° symmetrically opposite thereto, blocked with an opaque material on the analyzer source side, and means electrically inverting and opposing signals of successive analytical and reference filters with the outputs contributed by their dummy counterparts during each rotation of said rotary filter wheel to thereby cancel the effects of said extraneous infrared radiation.

9. The method of compensating rotary filter type infrared radiation photometric analyzers for extraneous infrared radiation contributed by apparatus elements according to claim 7 wherein preselected modulated reference or analytical radiation signals are also cancelled by electrical inversion and opposition techniques.

10. Apparatus according to claim 8 provided with means for cancelling a preselected one of the reference and analytical radiation components by electrical inversion and opposition techniques.

* * * * *